US011383024B2

(12) United States Patent
Cottin et al.

(10) Patent No.: US 11,383,024 B2
(45) Date of Patent: Jul. 12, 2022

(54) SYSTEM FOR PROVIDING MULTIPLE INFUSIONS TO A PATIENT

(71) Applicant: Fresenius Vial SAS, Brézins (FR)

(72) Inventors: Pauline Cottin, Voiron (FR);
Alexandre Guerrini, Fontaine (FR);
Frank Doesburg, Groningen (NL);
Maarten Nijsten, Groningen (NL)

(73) Assignee: Fresenius Vial SAS, Brézins (FR)

( * ) Notice: Subject to any disclaimer, the term of this patent is extended or adjusted under 35 U.S.C. 154(b) by 273 days.

(21) Appl. No.: 16/623,556

(22) PCT Filed: May 29, 2018

(86) PCT No.: PCT/EP2018/064066
§ 371 (c)(1),
(2) Date: Dec. 17, 2019

(87) PCT Pub. No.: WO2019/001879
PCT Pub. Date: Jan. 3, 2019

(65) Prior Publication Data
US 2021/0146037 A1    May 20, 2021

(30) Foreign Application Priority Data
Jun. 30, 2017 (EP) ...................................... 17305831

(51) Int. Cl.
*A61M 5/14* (2006.01)
*G16H 20/17* (2018.01)
(Continued)

(52) U.S. Cl.
CPC .......... *A61M 5/1408* (2013.01); *A61M 5/145* (2013.01); *A61M 5/1415* (2013.01);
(Continued)

(58) Field of Classification Search
None
See application file for complete search history.

(56) References Cited

U.S. PATENT DOCUMENTS 4,925,444 A * 5/1990 Orkin ................ A61M 5/16827
123/DIG. 13
6,070,761 A    6/2000 Bloom et al.
(Continued)

FOREIGN PATENT DOCUMENTS

AU    1999 29073 A1    12/1999
CN    101267854    9/2008
(Continued)

OTHER PUBLICATIONS

International Search Report and Written Opinion, counterpart International Appl. No. PCT/EP2018/064066 (dated Jun. 25, 2018) (17 pages).
(Continued)

*Primary Examiner* — Manuel A Mendez
(74) *Attorney, Agent, or Firm* — Cook Alex Ltd.

(57) ABSTRACT

A system for providing multiple infusions to a patient (P), the system comprises a multiplicity of infusion devices (10) for administering a multiplicity of medical fluids through an infusion line (102) of an infusion set (103) to the patient (P), and a control device (2) for controlling the multiplicity of infusion devices (10). Herein, the control device (2) comprises a multiplex module (22) configured to multiplex the multiplicity of medical fluids for a multiplexed administration of the medical fluids through said infusion line (102) of the infusion set (103), the multiplex module (22) comprising a scheduling module (222) configured to define at least two packets, each packet comprising at least one medical fluid out of the multiplicity of medical fluids, and to arrange the at least two packets in a sequence for administration of the medical fluids of the at least two packets. In this way a
(Continued)

system for providing multiple infusions to a patient is provided which allows for an efficient, yet reliable administration of multiple infusions while at the same time reducing the risks for errors. An advantage of multiplexing is reduction of the number of lumens with associated reduction of infection risks and discomfort.

19 Claims, 6 Drawing Sheets

(51) Int. Cl.
  *G16H 40/63* (2018.01)
  *A61M 5/145* (2006.01)
  *A61M 5/168* (2006.01)
  *A61M 5/172* (2006.01)
(52) U.S. Cl.
  CPC ........ *A61M 5/16827* (2013.01); *A61M 5/172* (2013.01); *G16H 20/17* (2018.01); *G16H 40/63* (2018.01)

(56) References Cited

U.S. PATENT DOCUMENTS

| | | | |
|---|---|---|---|
| 6,117,103 | A | 9/2000 | Tverskoy et al. |
| 7,895,053 | B2 | 2/2011 | Holland et al. |
| 2002/0143580 | A1* | 10/2002 | Bristol .................. G16H 40/67 705/2 |
| 2006/0287884 | A1* | 12/2006 | Sandy .................. G16H 70/40 705/2 |
| 2009/0177188 | A1 | 7/2009 | Steinkogler |
| 2010/0318062 | A1 | 12/2010 | Lauer et al. |
| 2011/0238032 | A1 | 9/2011 | McTaggart et al. |
| 2014/0278122 | A1 | 9/2014 | Naker et al. |
| 2014/0297313 | A1 | 10/2014 | Condurso et al. |
| 2016/0256622 | A1 | 9/2016 | Day et al. |

FOREIGN PATENT DOCUMENTS

| | | |
|---|---|---|
| CN | 101861587 | 10/2010 |
| CN | 105229648 | 1/2016 |
| JP | 2000-513259 | 10/2000 |
| JP | 2013-521993 | 6/2013 |
| WO | WO 2014/190200 A1 | 11/2014 |
| WO | WO 2014/210465 A1 | 12/2014 |
| WO | WO 2016/173843 A1 | 11/2016 |
| WO | WO2016/196098 | 12/2016 |

OTHER PUBLICATIONS

Liu et al., Scheduling Algorithms for Multiprogramming in a Hard-Real-Time Environment, Assoc. for Computing Machinery (1973) (15 pages).

Search Report, counterpart Chinese App. No. 201880042034.3 (dated Jun. 27, 2021) (2 pages).

Office Action, counterpart Chinese App. No. 201880042034.3 (dated Jul. 1, 2021) (13 pages) (with English translation).

Search Report, counterpart Japanese App. No. 2019-571230, with English translation (dated Feb. 16, 2022) (28 pages).

Notice of Reasons for Refusal, counterpart Japanese App. No. 2019-571230, with English translation (dated Feb. 22, 2022) (10 pages).

* cited by examiner

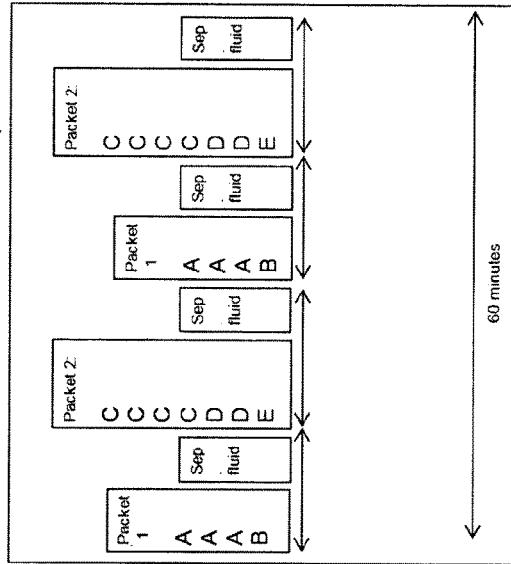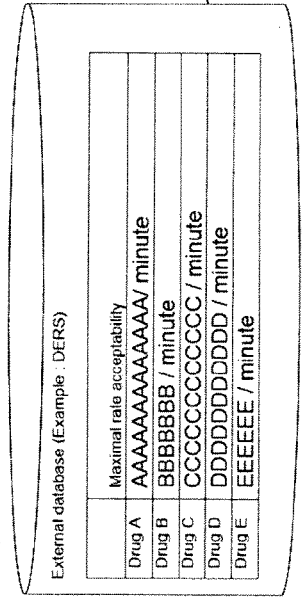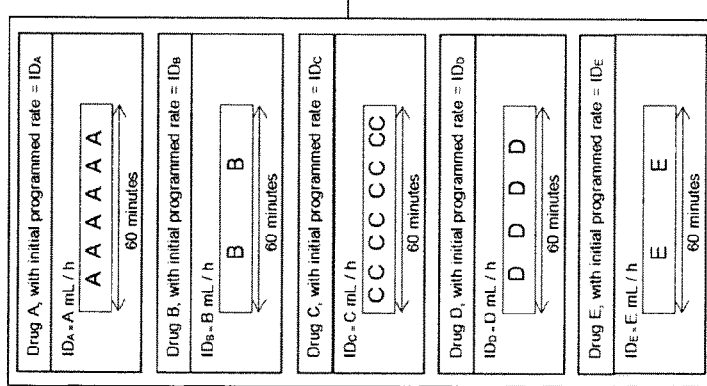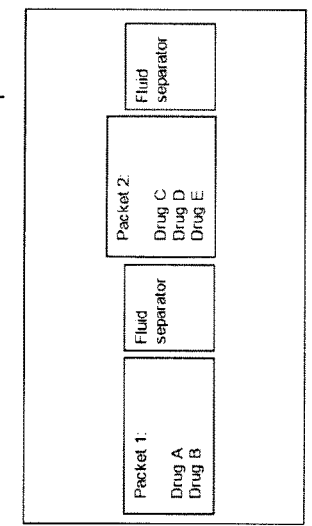
FIG 6

SYSTEM FOR PROVIDING MULTIPLE INFUSIONS TO A PATIENT

The present application is a U.S. National Stage of PCT International Patent Application No. PCT/EP2018/064066, filed May 29, 2018, which claims priority to EP Application No. 17305831, filed Jun. 30, 2017, both of which are hereby incorporated herein by reference.

The invention relates to a system for providing multiple infusions to a patient according to the preamble of claim 1 and to a method for providing multiple infusions to a patient.

A system of this kind comprises a multiplicity of infusion devices for administering a multiplicity of medical fluids through an infusion line of an infusion set to the patient, and a control device for controlling the multiplicity of infusion devices.

Intravenous (IV) therapy is one of the most common forms of treatment in hospitals worldwide. Using an infusion pump, medical solutions such as drug solutions are delivered into the bloodstream of a patient at a preprogrammed rate. In many places where complex care is provided, such as in intensive care units (ICU), patients typically receive IV treatment using multiple infusion pumps. As many drugs are chemically incompatible, drugs are often administered through separate infusion lines (lumens) in order to avoid precipitation or inactivation. When the number of available lumens is too low to facilitate the safe administration of these drugs, additional (peripheral) catheters need often to be placed, causing physical discomfort for the patient and introducing additional risks.

In neonatal intensive care units (NICUs) for example, catheter related complications can potentially decrease the already limited number of usable catheter sites.

Conventional multi-infusion therapy involves the manual operation of multiple infusion pumps, often in a hectic work environment. Such pumps may be complex to operate individually, and within a multi-infusion therapy their use must be aligned and harmonized, which potentially is prone to human error and therefore comes with a risk of medication errors. The multitasking involved with the simultaneous operation of multiple infusion pumps also increases the work load of an ICU nurse and thereby the likelihood of errors.

There hence is a desire to be able to administer multiple infusions to a patient in a coordinated, harmonized fashion while at the same time reducing the risk for errors and the strain on a user.

US 2014/0297313 A1 discloses a system and method of managing therapy provided to patients in an institution. The system herein monitors all aspects of the medication delivery to a patient, as well as other information related to the patient, such as values of vital signs, laboratory results and patient factors such as history, diagnoses, allergies and the like. US 2014/0297313 A1 herein describes that infusions of two infusates can be performed using a single infusion device via a Y-site connector. The setup of such infusions may employ a checking for compatibility of medical solutions to be infused via the Y-site connector, an alarm being issued if an incompatibility of medical solutions is detected.

U.S. Pat. No. 7,895,053 describes a medication management system including a medication management unit associated with a medical device. The medication management unit downloads medication delivery code based on a medication delivery order to the medical device only if the information from a first input matches information from a second input.

U.S. Pat. No. 6,070,761 describes a system capable of preparing and delivering one or multiple intravenous drugs to a patient.

It is an object of the instant invention to provide a system and method for providing multiple infusions to a patient which allow for an efficient, yet reliable administration of multiple infusions while at the same time reducing the risks for errors.

This object is achieved by a system comprising the features of claim 1.

Herein, the control device of the system comprises a multiplex module configured to multiplex the multiplicity of medical fluids for a multiplexed administration of the medical fluids through said infusion line of the infusion set, the multiplex module comprising a scheduling module configured to define at least two packets, each packet comprising at least one medical fluid out of the multiplicity of medical fluids, and to arrange the at least two packets in a sequence for administration of the medical fluids of the at least two packets.

Accordingly, infusions shall be multiplexed for administration to a patient. Herein, for administering the infusions a (single) infusion line having a (single) lumen may be employed, the multiple infusions being administered via the lumen towards the patient. Hence, for the administration of the multiple infusions a single port such as a catheter or the like may be used, hence reducing the number of ports to be provided on a patient and hence increasing the patient's comfort.

For administering the multiple infusions to the patient, the control device (in a setup phase) shall define a sequence of packets of medical solutions. The control device herein is configured to define packets, each packet comprising one or multiple medical solutions which, within the packet, shall be administered in parallel.

A packet in this context generally is thus to be understood as a combination of any number of medical solutions, in particular drug solutions, intended to be infused to the patient in parallel via the infusion line. By forming packets, hence, multiple (compatible) medical solutions may be administered to the patient in parallel and hence in an effective manner, multiple packets being arranged in a sequence such that, during the actual administration, one packet of medical solutions after another is administered to the patient.

For example, a first packet may be defined to comprise drug solutions A and B, whereas a second packet may be defined to comprise drug solution C. In the sequence, the first packet comprising drug solutions A and B may be placed first, followed by the second packet comprising drug solution C. During the actual administration, then, first drug solutions A and B are administered in parallel for a predefined duration, followed by the administration of the second packet comprising drug solution C for another predefined duration.

During the actual administration, the control device may control the administration of the sequence of packets in a repetitive fashion, such that the administration of the sequence is repeated for a predefined number of times until the administration of the medical solutions is completed.

In one embodiment, at least one packet comprises at least two medical fluids to be administered to the patient in parallel. Beneficially, each packet comprises at least two medical fluids to be administered to the patient in parallel. It however is also conceivable that a packet may be defined to comprise only a single medical solution.

As a general approach, in one embodiment packets may be defined to comprise a largest possible combination of medical solutions to be administered to the patient in parallel, the largest possible combination being dependent on constraints such as a maximum number of medical solutions to be grouped together in a packet for parallel administration, a packet utility value, and/or compatibility constraints.

In one embodiment, the multiplex module of the control device may comprise an analyzing module configured to determine, using information obtained from a database, whether medical fluids of the multiplicity of medical fluids are compatible for administration to the patient in parallel, wherein the scheduling module is configured to group at least two compatible medical fluids together to define a packet. Within the database it is stored and defined whether different medical solutions are compatible with one another or not. For example, the database defines whether drug solution A is compatible with drug solutions B, C, D, and E, and so on, such that the different drugs may be administered together via a single infusion line (or not). The defining of packets takes the compatibility of medical solutions into account in that only such medical solutions may be grouped together in a packet which are compatible and hence which may be administered to the patient in a parallel fashion, i.e. synchronously via the same infusion line comprising a single lumen and providing a single access to the patient.

If it is found that medical solutions are compatible, such medical solutions may be grouped together in a packet, wherein in principle as many medical solutions as are compatible may be grouped together in a packet, potentially subject to further constraints. If it is found that medical solutions are not compatible, they are placed in different packets and hence are not administered to the patient in parallel, but sequentially in the sequence of packets defined by the multiplex module.

In another aspect, the scheduling module may further be configured to obtain, from a database, information relating to permissible interruption times of medical fluids of the at least two packets. The interruption time is defined as the time period for which the administration of a medical solution may be temporarily stopped while having no (or at least insignificant) therapeutic impact as compared to a continuous infusion. The interruption time of a medical solution hence defines an admissible gap in between two instances of administration of a medical solution. The interruption time is correlated to the period of the (periodic) administration of the medical solution, the period is derived from the administration duration and the interruption time.

In one embodiment, based on the interruption times of the medical fluids grouped together in a packet, a packet interruption time relating to the entire packet is defined. For example, the packet interruption time may be defined as the smallest of the permissible interruption times of the medical fluids contained in the packet.

If the packet interruption time for a packet is known, it is known what time is available in between two instances of that packet, which may be used for administration of one (or multiple) other packets. Hence, in one embodiment, the duration of a packet, which is the duration of administration of the packet within the sequence, may be determined based on an administration time assigned to at least one medical fluid of the packet or a permissible interruption time assigned to at least one medical fluid of another packet, in particular the packet interruption time of the other packet. The duration of the packet in particular may be determined to correspond to the packet interruption time of another packet, such that the packet may fit in between the instances of the other packet (if e.g. two packets are present within the sequence).

In another aspect, the scheduling module of the multiplex module may be configured to determine a utility value for the sequence of packets based on the durations of the packets and interruption times of the packets. In particular, for calculating the utility value the following formula may be employed:

$$U = \sum_{i=1}^{n} \frac{D_i}{P_i},$$

wherein U is the utility value, $D_i$ is the duration of the i-th packet (out of n packets), and $P_i$ is the time period of the i-th packet in which the i-th packet will be scheduled at least once. $P_i$ is derived from the duration of the i-th packet and the interruption time $I_i$ of the i-th packet ($P_i = D_i + \frac{1}{2}I_i$). The duration, period and packet interruption time may for example, in this equation, be expressed in seconds, minutes, or hours, but should each use the same unit.

Generally, the relation between the period, duration and interruption time is defined as $I_i = 2(P_i - D_i)$. Hence, $P_i = D_i + \frac{1}{2}I_i$.

The determination of a utility value is inspired by computer technology in which a multi-program scheduling on a single processor may be assessed using a utility value, as described by C. L. Liu and J. W. Leyland in "Scheduling algorithms for multiprogramming in a hard-real-time environment". Association for Computing Machinery, 1973; 20:46-61. The utility value expresses, with respect to computer science, the fraction of processor time spent in the conclusion of a task set. Transferred to the instant subject of multiplex infusion, the utility value expresses the fraction of use of the (single) infusion line for administration of multiple medical solutions in a coordinated, harmonized fashion, i.e. in a sequential administration of multiple packets of multiple medical solutions (to be administered in parallel within a packet).

The utility value in particular may provide a constraint for defining the packets. In particular, if it is found that the utility value for the sequence of packets exceeds a threshold, for example having the value 1 or 1.2, this indicates that the sequence of packets cannot be administered using a single infusion line having a single lumen and providing a single access to the patient, such that the packets within the sequence must be redefined, for example by removing one or multiple medical fluids from one or multiple packets of the sequence. In a particular example, the medical solution having the smallest period or interruption time may be selected to be removed from the associated packet, this medical solution then having to be administered through a different lumen (of the same or another infusion line).

Generally, a utility value of 1 allows for a feasible schedule. In general, the utility value should be smaller than or equal to 1 to create a feasible schedule.

Upon redefining the sequence of packets, the utility value is calculated anew, wherein the redefinition of the sequence of packets may be repeated until a utility value below the threshold, in particular below or equal to 1, is obtained.

In another aspect, the scheduling module of the multiplex module may further be configured to assign a flow rate to each of the medical fluids of the at least two packets based on the duration of the packet to which the medical fluid is assigned. Generally, for each medical fluid the volume to be infused to the patient is known. Furthermore, the duration of administration of the packet the medical fluid is associated with within the sequence is known, and the number of repetitions of the sequence, i.e. the total duration of administration of all instances of the sequence of packets, is known. Hence, for each medical fluid the flow rate for administration during each instance of the packet may be determined by dividing the total volume of the medical solution to be infused by the time of administration, which corresponds to the combined duration of all instances of the packet the medical solution is associated with.

Having defined the flow rate, during the actual administration the infusion device associated with the medical solution may be controlled suitably such that during an instance of the packet the medical solution is administered with said flow rate.

After having defined the packets (each packet comprising one or multiple medical solutions) the packets are arranged in a sequence, according to which the infusion devices then may be controlled for the actual administration. For placing the packets in the sequence, in particular for determining the order of the packets in the sequence, the packets may be prioritized, which may take place by assigning a priority to each packet for example based on an administration deadline of a medical fluid of the packet, and placing the packets in the sequence according to their priority. For example, the packet comprising the medical solution having the earliest administration deadline may be placed first in the sequence, followed by the packet comprising the medical solution with the next urgent administration deadline.

The packets in particular are defined by grouping compatible medical solutions together. Hence, different packets may comprise medical solutions which are incompatible with each other, hence requiring a sufficient separation between the packets during the sequential administration. For this, a separator fluid may be arranged in the sequence in between packets having incompatible medical solutions, such that a fluid separation between the packets is obtained. The separator fluid may in particular be a neutral, solution that does not contain a drug such as a saline (NaCl) solution or a glucose solution. The separator fluid however may also be another packet comprising medical solutions being compatible to the medical solutions of the packet before and the packet after.

If a separator fluid is inserted in between two packets, this has to be taken into account when for example determining the duration of a packet and the utility value of the sequence. In particular, the duration of the entire packet has to include the duration of the separator fluid administration, hence less time being available for administering the medical fluids of the packet.

During the actual administration, the control device, according to another aspect, is configured to control the multiplicity of infusion devices for administering the sequence of packets of medical fluids to the patient. The definition of the packets and the forming of the sequence takes place in a setup phase prior to the actual infusion, and upon having defined the sequence of packets for administration the actual administration may be started by controlling the infusion devices to infuse the medical fluids of the packets according to the sequence of packets and their grouping together in the packets.

The infusion devices may in particular be infusion pumps such as a volumetric infusion pumps or syringe infusion pumps. Multiple infusion devices herein may be organized for example at the bedside of a patient on an organization device such as a rack constituted to mechanically hold the infusion devices and to communicatively link the infusion devices to each other and to the control device.

The control device may for example be a so called infusion manager which may be communicatively linked to the infusion devices. The communication link herein may be a wired communication link, such as a wired network link, or a wireless communication link, for example according to the WiFi or Bluetooth standard.

The control device may for example be a computing device such as a personal computer (PC), a tablet computer or a mobile computing device such as a smart phone or the like. The control device for example may run software implementing the multiplex module, including the scheduling module and the analyzing module, which hence not necessarily are separate hardware units, but may be implemented in software within the control device.

The control device may be linked to an external database, for example implemented on an external server within a hospital network or the like. The database, in particular comprising information with regard to compatibility of different medical solutions such as drug solutions, permissible interruption times of medical solutions and the like, may for example be an SQL database.

The object is also achieved by means of a method for providing multiple infusions to a patient, the method comprising: controlling, using a control device, a multiplicity of infusion devices for administering a multiplicity of medical fluids through an infusion line of an infusion set to the patient. Herein, in a set-up phase, using a multiplex module of the control device the multiplicity of medical fluids are multiplexed for a multiplexed administration of the medical fluids through said infusion line of the infusion set in that the multiplex module defines at least two packets, each packet comprising at least one medical fluid out of the multiplicity of medical fluids, and arranges the at least two packets in a sequence for administration of the medical fluids of the at least two packets.

The advantages and advantageous embodiments described above for the system equally apply to the method, such that it shall be referred to the above.

The method in particular is executed on the control device in a setup phase prior to the actual administration of the medical solutions to the patient. The definition of the packets and the arranging of packets in a sequence hence serves to configure a multiplex infusion operation for administration to the patient. Upon completion of the setup phase the actual administration may be started such that the multiple medical solutions are administered to the patient according to the sequence of packets as defined during the setup phase.

The idea underlying the invention shall subsequently be described in more detail according to the embodiments shown in the figures. Herein:

FIG. 6 shows a flow chart of a subsequent step during the setup of the infusion devices.

Figure 1:
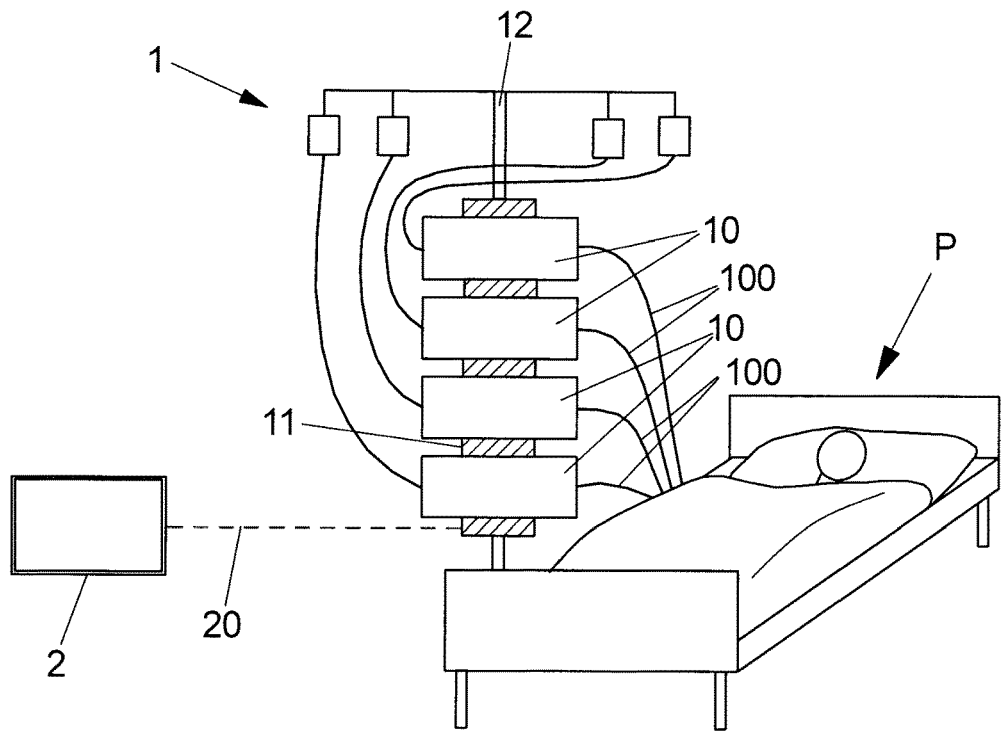
FIG. 1 shows a schematic drawing of a scenario as it can be found at the bedside of a patient in a hospital environment, for example in an intensive care unit.

Referring to the schematic view of FIG. 1, in a hospital environment multiple infusion devices 10 may be arranged at the bedside of a patient P for administering multiple medical solutions to the patient P. A scenario of this kind may for example be found in a critical care unit of a hospital, for example an intensive care unit, wherein the orchestrated, coordinated administration of multiple medical solutions to the patient P may be critical to sustain the patient's constitution.

The infusion devices 10, for example in the form of volumetric (peristaltic) or syringe infusion pumps, may for example be arranged on a rack 11, which is constituted to mechanically hold the infusion devices 10 in an organized fashion and to provide a communication backbone in between the infusion devices 10, also connecting the infusion devices 10 to an external communication network, for example a hospital network.

The rack 11 is arranged on a stand 12 and in this way is physically placed at the bedside of the patient P.

In the instant scenario, the infusion devices 10 are controlled by a control device 2 being linked for example to the rack 11 and via the rack 11 to the infusion devices 10 by means of a communication link 20, for example a wired link or a wireless link. The control device 2 may be implemented for example on a computing device, such as a personal computer, a tablet computer, a laptop computer, a mobile device such as a smart phone, or the like. The control device 2 may be a dedicated physical entity, or alternatively may be implemented by software on a multipurpose computing device.

Figure 2:
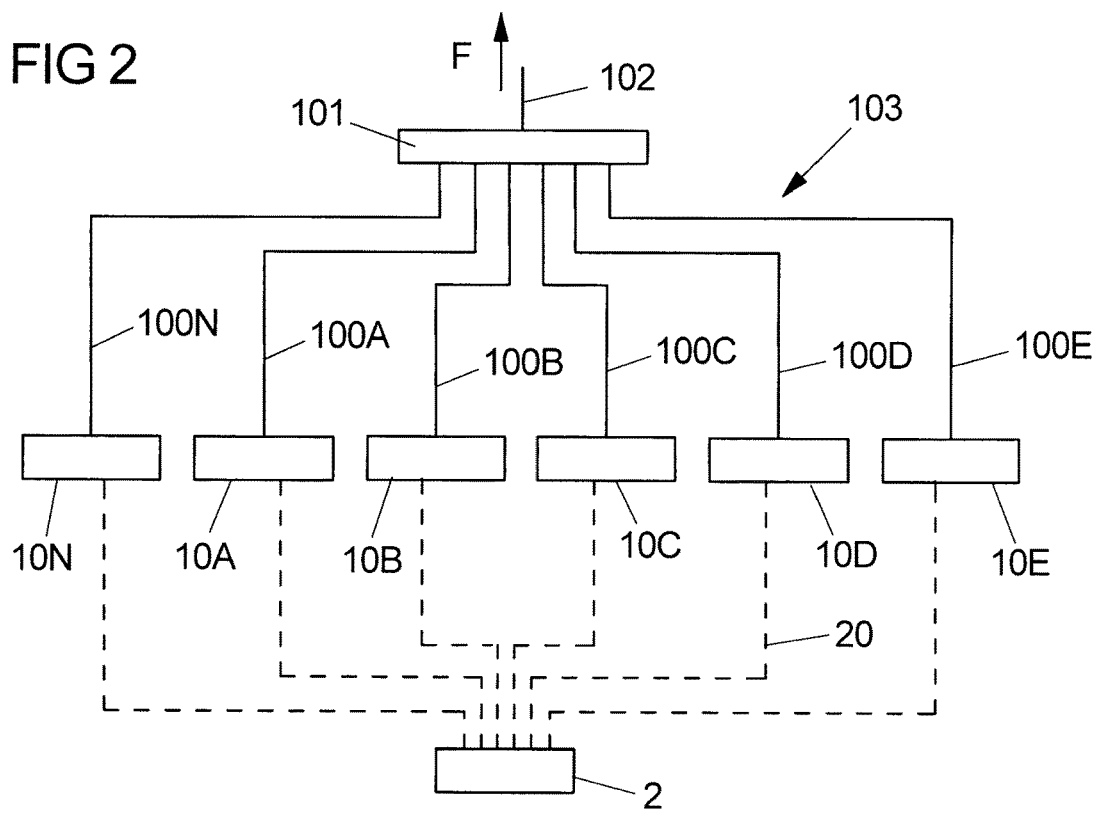
FIG. 2 shows a schematic view of an arrangement of multiple infusion devices for administering multiple medical solutions to a patient.

Within the instant context, the control device 2 controls the infusion devices 10 for an orchestrated infusion of multiple medical solutions. Herein, as illustrated in FIG. 2, the infusion devices 10A, 10B, 10C, 10D, 10E, 10N may be connected to a connection device 101 via the delivery lines 100A, 100B, 100C, 100D, 100B, 100N, the connection device 101 for example comprising switchable valves for switching between infusions of the different infusion devices 10A, 10B, 10C, 10D, 10E, 10N for delivery via a single infusion line 102 connected to the patient P. Hence, multiple infusions of the multiple infusion devices 10A, 10B, 10C, 10D, 10E, 10N may be applied to the patient P via a single infusion line 102 having a single lumen and providing single access to the patient P.

Figure 3:
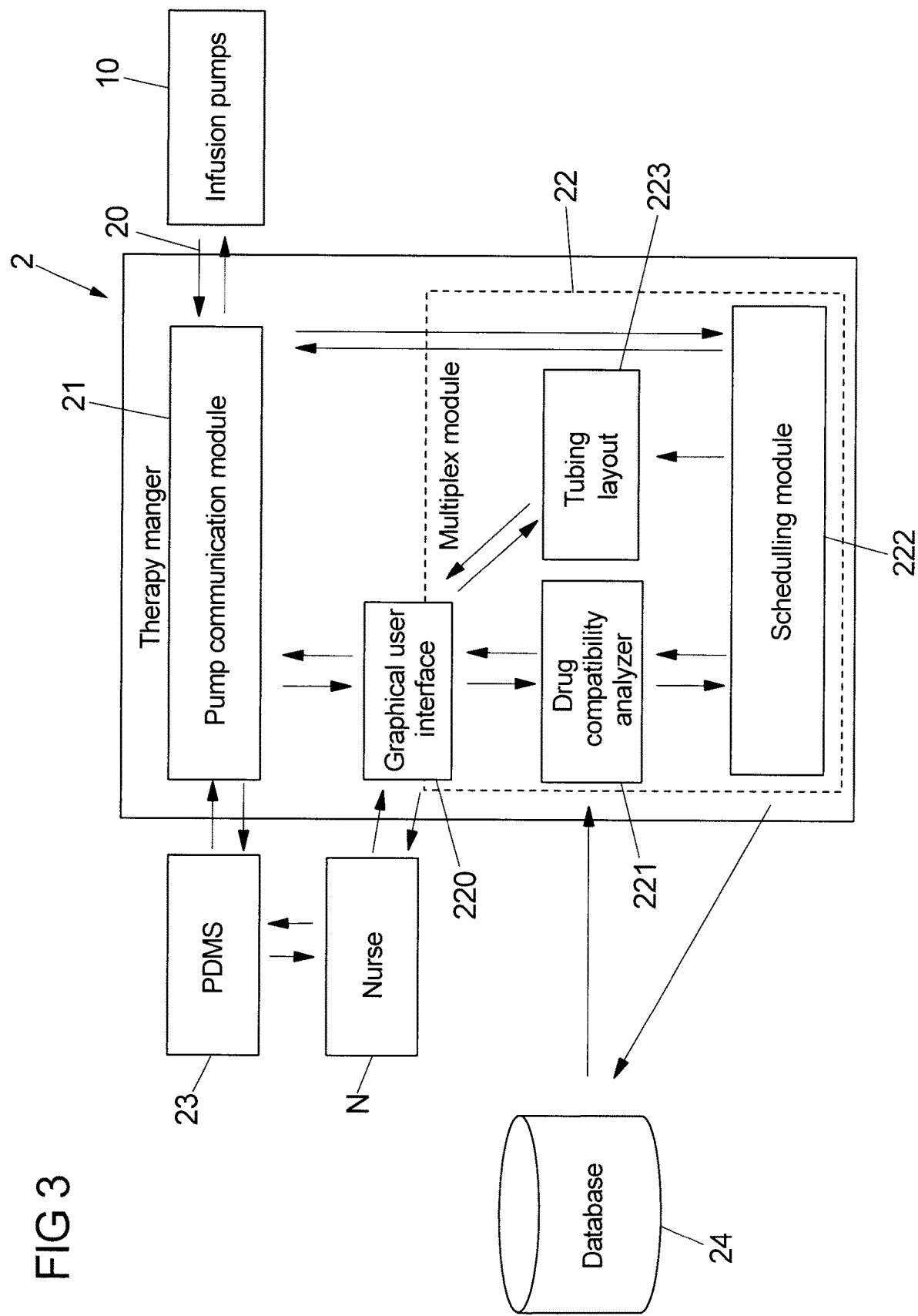
FIG. 3 shows a schematic functional drawing of a control device for controlling multiple infusion devices.

Referring now to FIG. 3, the control device 2, in one embodiment, comprises a communication module 21 for communicating to the infusion devices 10 and for communicating for example to a patient data management system (PDMS) 23 of the hospital. The communication module 21 may be configured for a wired communication via a wired network connection, or for a wireless communication for example according to the WiFi or the Bluetooth standard. Via the communication module 21 information may be received from the infusion devices 10 or the patient data management system 23, and commands may be issued for example to the infusion devices 10 for controlling their operation.

The control device 2 furthermore comprises a multiplex module 22 which serves to multiplex the administration of multiple medical solutions to the patient P. The multiplex module 22, which may be a separate physical entity or which may be implemented by software including all its components within a computing device implementing the control device 2, comprises a (graphical) user interface 220 via which a user N, for example a nurse, may interact with the control device 2 and may input control commands, such as information relating to medical solutions to be infused to a patient P.

The multiplex module 22 furthermore comprises a scheduling module 222 which serves to define packets of medical solutions to be administered in parallel to the patient P and to arrange the packets in a sequence for the administration to the patient P, as shall be in more detail described below.

An analyzing module 221 serves to analyze compatibilities/incompatibilities between the different medical solutions and provides its input in particular to the scheduling module 222 for defining packets of medical solutions.

A layout module 223 contains information relating to the layout of a tubing set 103 comprising delivery lines 100A, 100B, 100C, 100D, 100E, 100N, the connection device 101 and the infusion line 102 as illustrated in FIG. 2, the layout module 223 for example allowing a user N to define, input and/or modify the layout of the lines of the infusion set 103 such that the layout may be taken into account for controlling the infusion operation.

The control device 2 interacts with a database 24, which may be internal to the control device 2 and for this may be implemented for example on a computing device also implementing the control device 2. The database 24 alternatively may be external to the control device 2 and may for example be stored on a server within a hospital network, the control device 2 being in communication connection with the database 24 for example via a hospital information network.

Figure 4:
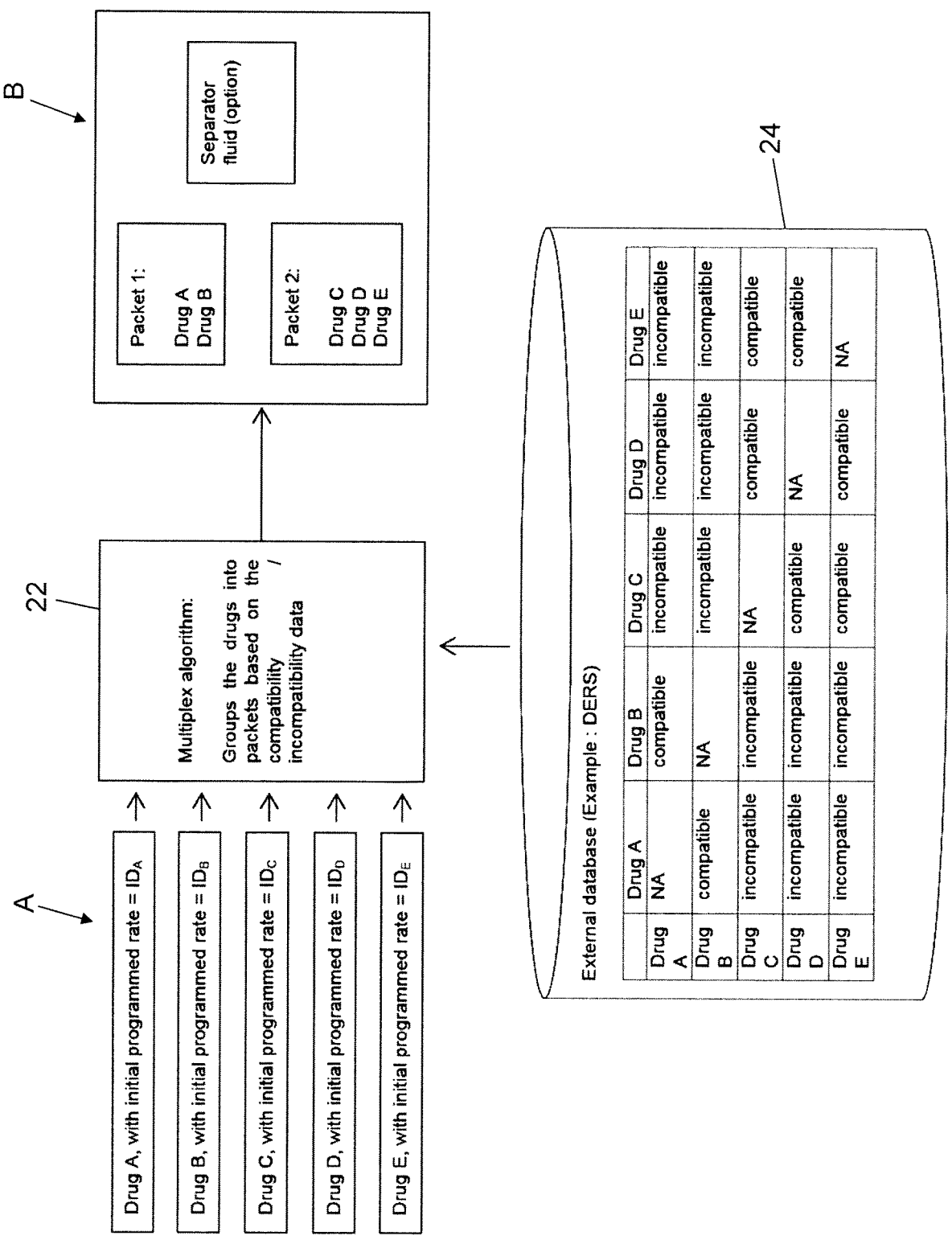
FIG. 4 shows a flow chart during a setup of multiple infusion devices for administering multiple medical solutions.
Figure 5:
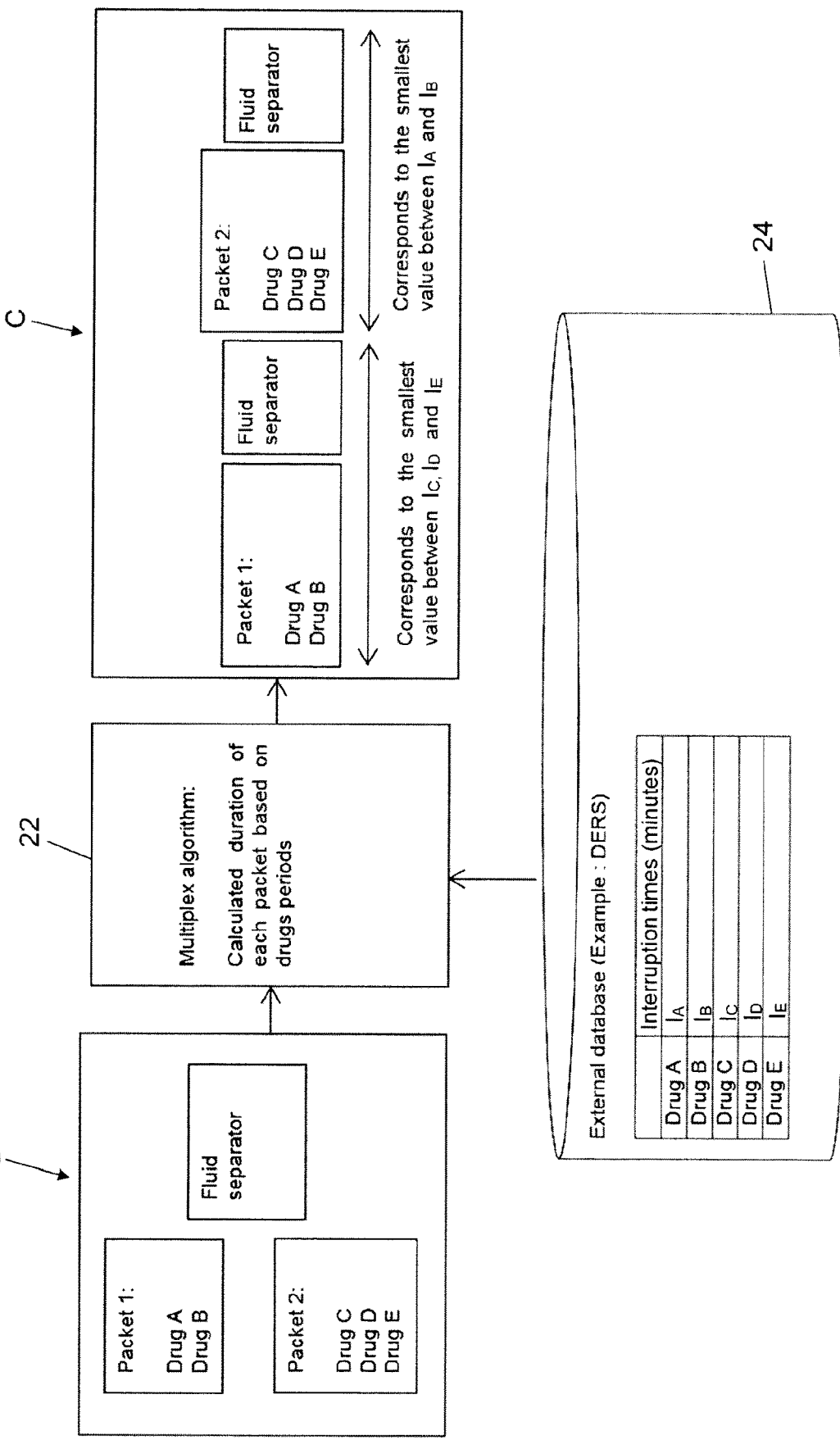
FIG. 5 shows a flow chart of a subsequent step during the setup of the multiple infusion devices.

As it is illustrated in FIGS. 4 to 6, the control device 2 serves to define a sequence of packets of medical solutions for a multiplexed administration of the medical solutions to the patient P, in a setup (programming) phase prior to the actual administration of the medical solutions to the patient P.

The process illustrated in FIGS. 4 to 6 serves to configure multiple infusion devices 10 for a multiplexed infusion of multiple medical solutions. At the start of the process, illustrated in FIG. 4, medical solutions are entered, for example by a user N, into the multiplex module 22 via for example the user interface 220 as input A, defining in the instant example five drugs, denoted as a drug A, drug B, drug C, drug D, and drug E.

When entering the different drugs into the control device 2, the user and may also indicate an initial programmed rate $ID_A$, $ID_B$, $ID_C$, $ID_D$, $ID_E$ for the administration of the different medical solutions.

Further to the definition of the different medical solutions, the multiplex module 22 takes as input from the external database 24 information with regard to the compatibilities/incompatibilities of the different medical solutions. The compatibilities/incompatibilities are for example defined in an association table stored in the database 24, the table defining whether a certain drug is compatible or incompatible with another drug, as illustrated in the bottom of FIG. 4.

In the example of FIG. 4, drug A is compatible with drug B, but is incompatible with drug C, drug D and drug E. This means, that drug A may be administered together with drug B, but may not be administered together with drug C, drug D and/or drug E, such that a sufficient separation of administration between drug A and drugs C, D and E must be provided. Likewise, drug B is compatible with drug A, but is incompatible with drug C, drug D and drug E. Drug C is incompatible with drugs A and B, but is compatible with drugs D and E. Drug D is incompatible with drug A and drug B, but is compatible with drug C and drug E. And drug E is incompatible with drug A and drug B, but is compatible with drug C and drug D.

Taking the input A and the compatibility/incompatibility information from the database 24, the multiplex module 22 defines packets of drugs which may be administered in parallel (i.e., synchronously) via a single infusion line. In the noted example, drugs A and B, which are compatible with each other, are grouped together in packet 1, whereas drugs C, D and E, which also are compatible with each other (but are incompatible with drugs A and B), are grouped together in packet 2 (output B).

In addition, during administration a separator fluid may have to be inserted in between the two packets in order to sufficiently separate the packets and their medical solutions from each other. The separator fluid may be a neutral fluid not containing a drug, such as a saline solution or a glucose solution, which may be administered, during the actual administration, using a dedicated infusion device 10N, as illustrated in FIG. 2. The separator fluid may also serve to flush the infusion line 102 in between the two packets during the actual administration.

Upon having defined the packets, which generally group drugs together for administration to the patient P, a sequence of the packets and their duration is determined, as this is illustrated in FIG. 5. Taking the general definition of the packets output in the step illustrated in FIG. 4 (output B) as input and obtaining as further input from the database 24 maximum permissible interruption times $I_A$, $I_B$, $I_C$, $I_D$, $I_E$ associated with the different drugs, durations for the different packets are determined.

Herein, for each packet a packet interruption time is determined as the smallest interruption time of the medical solutions grouped together in the packet. From the packet interruption time of the first packet the duration of the other, second packet is derived, the duration of the second packet (including the required duration for the separator fluid) being determined to correspond to the packet interruption time of the first packet, and vice versa.

The permissible interruption time of a medical fluid generally indicates for what maximum time period the administration of a medical solution may be interrupted without having a significant (disadvantageous) therapeutic effect. Hence, the packet interruption time indicates a permissible pause between two instances of a packet, which may be used for administering another packet of medical solutions.

The duration of administration of the separator fluid may be predefined, assuming for example a maximum flow rate and a minimum volume of separator fluid to provide for a sufficient separation. The actual duration available for administering the medical fluids of a packet, in the instant example comprising two packets, then will equal the packet interruption time of the other packet minus the duration of the administration of the separator fluid.

Having determined the durations of the packets, the general set up of a sequence of packets is obtained as output C, as illustrated in FIG. 5.

In a next step, a utility value is calculated for the sequence responding to output C, the utility value generally being calculated according to the following formula:

$$U = \sum_{i=1}^{n} \frac{D_i}{P_i},$$

wherein U is the utility value, $D_i$ is the duration of the i-th packet out of n packets, and $P_i$ is the time period of the i-th packet in which the i-th packet will be scheduled at least once. $P_i$ is derived from the duration of the i-th packet and the interruption time of the i-th packet.

The utility value indicates the fraction of use of the single lumen infusion line 102 for administering the sequence of packets comprising the different medical solutions. A utility value smaller than or equal to 1 indicates that the sequence of packets may sequentially be administered using the single infusion line 102. A utility value larger than 1 indicates that more than one infusion line 102, i.e., more than one lumen, is required for administering the medical solutions to the patient.

The above formula as such does not take the separator fluid into account. If a separator fluid has to be inserted in between packets, the calculation of the utility value may take place using the following formula:

$$U = \sum_{i=1}^{n} \frac{D_i + D_{sep}}{P_i - D_{sep}},$$

in which $D_{sep}$ indicates the duration of administration of the separator fluid in between the packets.

If, for the sequence determined as output C in the flow chart of FIG. 5, a utility value larger than 1 arises, the packets need to be redefined. For this, the medical solution having the smallest interruption time is removed from the associated packet and is indicated to the user N to be infused via a separate infusion line 102 (or another lumen of the same infusion line 102). After removal of the noted medical solution, the utility value is recalculated, potentially repeating the procedure until a utility value smaller than or equal to 1 is obtained, indicating that the now obtained sequence of packets may be administered to the patient using a single infusion line 102.

As illustrated in the flow chart of FIG. 6, the definition of the sequence of packets obtained as output C in FIG. 5 (after the optimization using the utility value) is taken as input in another step during which the flow rates of the medical solutions of the packets for the administration using the infusion devices 10 are determined. Herein, from the initial programmed rate and the known time of administration, the volume of administration for each medical solution is known (input D in the flow chart of FIG. 6). From the known volume of each medical solution and from the combined duration of the packets within a repetitive administration of the sequence of packets it hence can be derived with which flow rate each medical solution is to be administered during the duration of the associated packet, as this is schematically illustrated in FIG. 6 (output E).

The initial programmed rates for the medical solutions hence are adapted, the infusion devices 10 being controlled according to the newly calculated flow rates during the later administration of the medical fluids within the sequence of packets.

As further illustrated in FIG. 6, as further input to the determination of the flow rates it is taken into account what maximal flow rates are acceptable for the different medical solutions, which is taken from the database 24. It generally is checked whether the determined flow rate exceeds the maximum permissible flow rate. If this is not the case, the determined flow rate is acceptable. If this is the case, the definition of the sequence of packets needs to be adapted, such that it must be reverted to the step illustrated in FIG. 5 for redefining the packets and their durations.

As illustrated also in FIG. 6, during the actual administration the sequence of packets shall be repeated, in the instant example, twice for an overall duration of 60 minutes. After completion of the repeated administration of the sequence of packets hence all medical solutions are in their desired volume administered to the patient P.

Prior to or after determining the flow rate, the order of the packets in the sequence is determined. This is done according to priority scheme taking an administration deadline of the medical fluids in the packets into account. Herein, a medical solution having an early deadline generally has a high priority, the packet associated with the medical solution having the highest priority (the shortest administration deadline) being placed first in the sequence. The deadline indicates how soon the administration of the medical solution should start: A short deadline indicates that the administration should start early, whereas a long deadline indicates that it can potentially be waited with administering the medical solution.

In the noted example, if for example drug A has the highest priority of all drugs contained in the sequence of packets of medical solutions, packet 1 is placed first in the sequence, followed by separator fluid and then packet 2.

Figure 7:
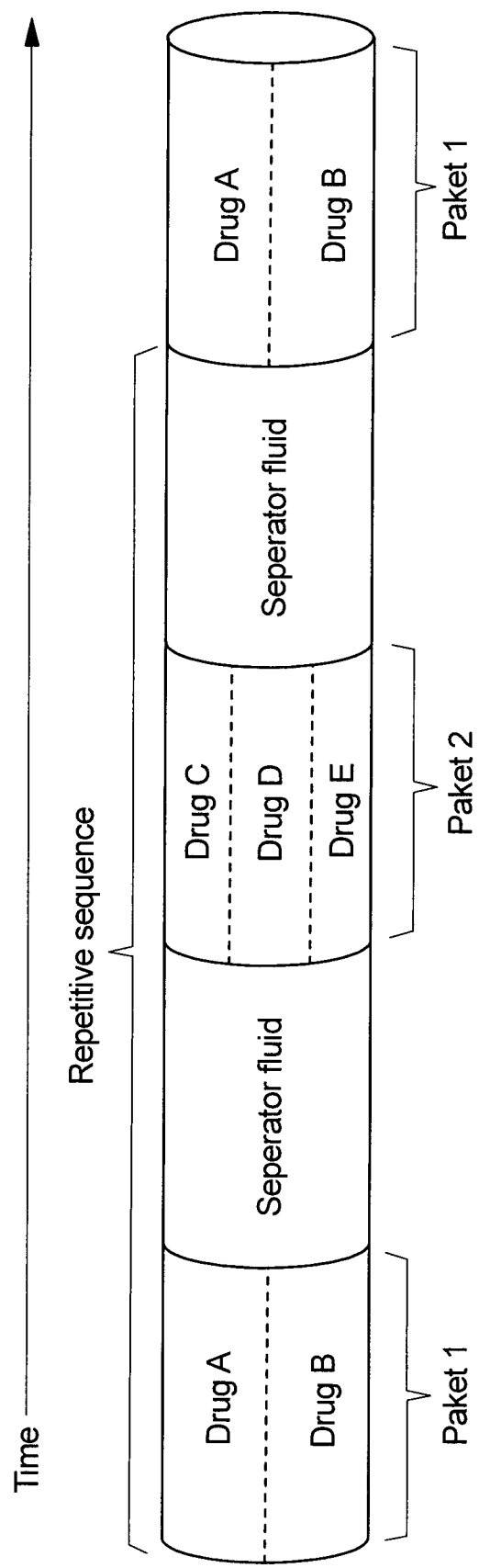
FIG. 7 shows an example of a sequence of packets of multiple medical solutions for administration to a patient.

As a result, as illustrated in FIG. 7, a repetitive sequence of packets for administration to the patient P is defined. The administration of the sequence herein takes place periodically, for a predefined number of repetitions of the sequence, such that each packet is administered multiple times to the patient P.

During the actual administration, the control device 2 controls the infusion devices 10A, 10B, 100, 10D, 10E in the setup of FIG. 2 to administer drug A, drug B, drug C, drug D and drug E according to the defined sequence of packets and the calculated flow rates, wherein in between two packets of incompatible medical solutions a separator fluid via the infusion device 10N may be administered.

The invention is not limited to the embodiments described above, but may be implemented in an entirely different fashion.

Using the described approach, medical solutions may be grouped together in packets for a multiplexed, parallel administration, wherein different packets of (incompatible) medical solutions may be defined for a sequential administration. Because medical solutions are administered in parallel, one packet of medical solutions being followed by the other, an efficient administration of multiple medical solutions in a multiplexed fashion becomes possible, hence potentially shortening an overall administration time of medical solutions to a patient.

Because the determination of a sequence of packets of medical solutions takes place automatically according to constraints defined in the system, the risk for human errors is reduced, enabling a reliable, efficient, secure administration of a multiplicity of medical solutions to a patient.

Another advantage of the proposed multiplexing scheme is that infection risks may be lowered by reducing the number of infusion lumens.

LIST OF REFERENCE NUMERALS

1 System
10, 10A-10E, 10N Infusion device
100, 100A-100E, 100N Delivery line
101 Connection member
102 Infusion line
103 Infusion set
11 Organization device (rack)
12 Stand
2 Control device
20 Communication connection
21 Communication module
22 Multiplex module
220 User interface
221 Analyzing module
222 Scheduling module
223 Layout module
23 Patient data management system
24 Database
A-E Input/output
F Flow
N User (nurse)
P Patient

The invention claimed is:

1. A system for providing multiple infusions to a patient, the system comprising:
   a multiplicity of infusion devices for administering a multiplicity of medical fluids through an infusion line of an infusion set to the patient, and
   a control device for controlling the multiplicity of infusion devices,
   wherein the control device comprises a multiplex module configured to multiplex the multiplicity of medical fluids for a multiplexed administration of the medical fluids through said infusion line of the infusion set, the multiplex module comprising a scheduling module configured to define at least two packets, each packet comprising operation of at least one of the multiplicity of infusion devices to administer at least one medical fluid out of the multiplicity of medical fluids, and to arrange the at least two packets in a repeating sequence for administration of the medical fluids of the at least two packets,
   wherein at least one packet of the at least two packets comprises simultaneous operation of two of the multiplicity of infusion devices to administer in parallel.

2. The system according to claim 1, wherein the multiplex module comprises an analyzing module configured to determine, using information obtained from a database, whether medical fluids of the multiplicity of medical fluids are compatible for administration to the patient in parallel, wherein the scheduling module is configured to group at least two compatible medical fluids together to define a packet.

3. The system according to claim 1, wherein the scheduling module is further configured to obtain, from a database, information relating to permissible interruption times of the medical fluids of the at least two packets.

4. The system according to claim 3, wherein the scheduling module is further configured to define, for each packet, a packet interruption time.

5. The system according to claim 4, wherein the packet interruption time is determined as a lowest of the permissible interruption times of the medical fluids of the packet.

6. The system according to claim 4, wherein the scheduling module is further configured to determine a duration of each packet based on an administration time assigned to at least one medical fluid of the packet and/or a permissible interruption time assigned to at least one medical fluid of another packet.

7. The system according to claim 6, wherein the scheduling module is further configured to determine a utility value for the sequence based on the durations of the packets and the interruption times of the packets.

8. The system according to claim 7, wherein the utility value is determined according to the following formula:

$$U = \sum_{i=1}^{n} \frac{D_i}{P_i}$$

wherein U is the utility value, $D_i$ is the duration of the i-th packet out of n packets, and $P_i$ is the time period of the i-th packet in which the i-th packet will be scheduled at least once, derived from the duration of the i-th packet and the interruption time of the i-th packet.

9. The system according to claim 7, wherein the scheduling module is further configured to suggest to remove at least one medical fluid from at least one packet if the utility value exceeds a threshold.

10. The system according to claim 6, wherein the scheduling module is further configured to assign a flow rate to each of the medical fluids assigned to the at least two packets based on the duration of the packet to which the medical fluid is assigned.

11. The system according to claim 1, wherein the scheduling module is further configured to assign a priority to each packet based on an administration deadline of a medical fluid of the packet, and placing the packets in the sequence according to their priority.

12. The system according to claim 1, wherein the scheduling module is further configured to place a separator fluid in between two neighboring packets for separating the administration of the medical fluids of the two neighboring packets from each other.

13. The system according to claim 1, wherein the control device is configured to control the multiplicity of infusion devices for administering the sequence of packets of medical fluids to the patient.

14. The system according to claim 1, wherein the control device is configured to determine the repeating sequence according to an interruption time for at least one medical fluid of each packet, the interruption time being an amount of time an infusion is temporarily stopped while having at least an insignificant therapeutic impact as compared to a continuous infusion.

15. A method for providing multiple infusions to a patient, the method comprising:
controlling, using a control device, a multiplicity of infusion devices for administering a multiplicity of medical fluids through an infusion line of an infusion set to the patient, and
multiplexing, in a set-up phase, using a multiplex module of the control device, the multiplicity of medical fluids for a multiplexed administration of the medical fluids through said infusion line of the infusion set in that the multiplex module defines at least two packets, each packet comprising operation of at least one of the multiplicity of infusion devices to administer at least one medical fluid out of the multiplicity of medical fluids, and arranges the at least two packets in a repeating sequence for administration of the medical fluids of the at least two packets,
wherein at least one packet of the at least two packets comprises operation of two of the multiplicity of infusion devices to administer in parallel.

16. The method according to claim 15, further comprising determining the repeating sequence according to an interruption time for at least one medical fluid of each packet, the interruption time being an amount of time an infusion is temporarily stopped while having at least an insignificant therapeutic impact as compared to a continuous infusion.

17. A system for providing multiple infusions to a patient, the system comprising:
a multiplicity of infusion devices for administering a multiplicity of medical fluids through an infusion line of an infusion set to the patient, and
a control device for controlling the multiplicity of infusion devices,
wherein the control device comprises a multiplex module configured to multiplex the multiplicity of medical fluids for a multiplexed administration of the medical fluids through said infusion line of the infusion set, the multiplex module comprising a scheduling module configured:
to define at least two packets, each packet comprising at least one medical fluid out of the multiplicity of medical fluids,
to obtain, from a database, information relating to permissible interruption times of the medical fluids of the at least two packets,
to define, for each packet, a packet interruption time,
to determine a duration of each packet based on an administration time assigned to at least one medical fluid of the packet and/or a permissible interruption time assigned to at least one medical fluid of another packet, and
to arrange the at least two packets in a sequence for administration of the medical fluids of the at least two packets,
wherein the scheduling module is further configured to determine a utility value for the sequence based on the durations of the packets and the interruption times of the packets.

18. The system according to claim 17, wherein the utility value is determined according to the following formula:

$$U = \sum_{i=1}^{n} \frac{D_i}{P_i}$$

wherein U is the utility value, $D_i$ is the duration of the i-th packet out of n packets, and $P_i$ is the time period of the i-th packet in which the i-th packet will be scheduled at least once, derived from the duration of the i-th packet and the interruption time of the i-th packet.

19. The system according to claim 17, wherein the scheduling module is further configured to suggest to remove at least one medical fluid from at least one packet if the utility value exceeds a threshold.

* * * * *